United States Patent [19]

Dori et al.

[11] Patent Number: 5,409,914

[45] Date of Patent: * Apr. 25, 1995

[54] METALLO-ORGANIC COBALT COMPOUNDS AND USES THEREOF

[75] Inventors: Zvi Dori, Haifa; David Gershon, Kiyat-Tavon, both of Israel

[73] Assignee: Chai-Tech Corporation, Greenvale, N.Y.

[*] Notice: The portion of the term of this patent subsequent to Sep. 17, 2008 has been disclaimed.

[21] Appl. No.: 146,395

[22] Filed: Nov. 1, 1993

Related U.S. Application Data

[60] Continuation of Ser. No. 895,526, Jun. 2, 1992, Pat. No. 5,258,403, which is a division of Ser. No. 606,070, Oct. 30, 1990, Pat. No. 5,142,076, which is a continuation of Ser. No. 279,417, Dec. 2, 1988, Pat. No. 5,049,557, which is a continuation-in-part of Ser. No. 147,713, Jan. 25, 1988, Pat. No. 4,866,054, and Ser. No. 147,714, Jan. 25, 1988, Pat. No. 4,866,053, each is a continuation-in-part of Ser. No. 862,804, May 13, 1986, abandoned.

[51] Int. Cl.$^6$ .................. A61K 31/555; A61K 31/295; C07F 15/06
[52] U.S. Cl. ..................... 514/185; 514/183; 514/188; 514/501; 514/825; 556/139; 556/146
[58] Field of Search ............... 514/501, 825, 183, 185, 514/188; 556/139, 146

[56] References Cited

U.S. PATENT DOCUMENTS

| | | | |
|---|---|---|---|
| 5,049,557 | 9/1991 | Dori et al. | 514/185 |
| 5,106,684 | 4/1992 | Scheer | 514/185 |
| 5,258,403 | 11/1993 | Dori et al. | 514/501 |

*Primary Examiner*—José G. Dees
*Assistant Examiner*—Porfirio Nazario-Gonzalez
*Attorney, Agent, or Firm*—McAulay Fisher Nissen Goldberg & Kiel

[57] ABSTRACT

The present invention provides a pharmaceutical composition of a complex compound having the structure:

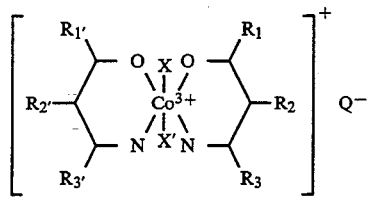

wherein $R_1$ and $R_{1'}$ are the same or different and each is an alkyl group, a phenyl group or a substituted derivative of a phenyl group;

wherein $R_2$ and $R_{2'}$ are the same or different and each is hydrogen, an unbranched alkyl group, a halide or a group having the structure

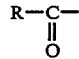

wherein R is hydrogen, an alkoxide group, an alkyl group, or OH;

wherein $R_3$ and $R_{3'}$ are the same or different and each is hydrogen or an alkyl group;

wherein X and X' are the same or different and each is a water soluble group having weak to intermediate ligand field strength; and Q is a soluble, pharmaceutically acceptable negative ion.

4 Claims, 5 Drawing Sheets

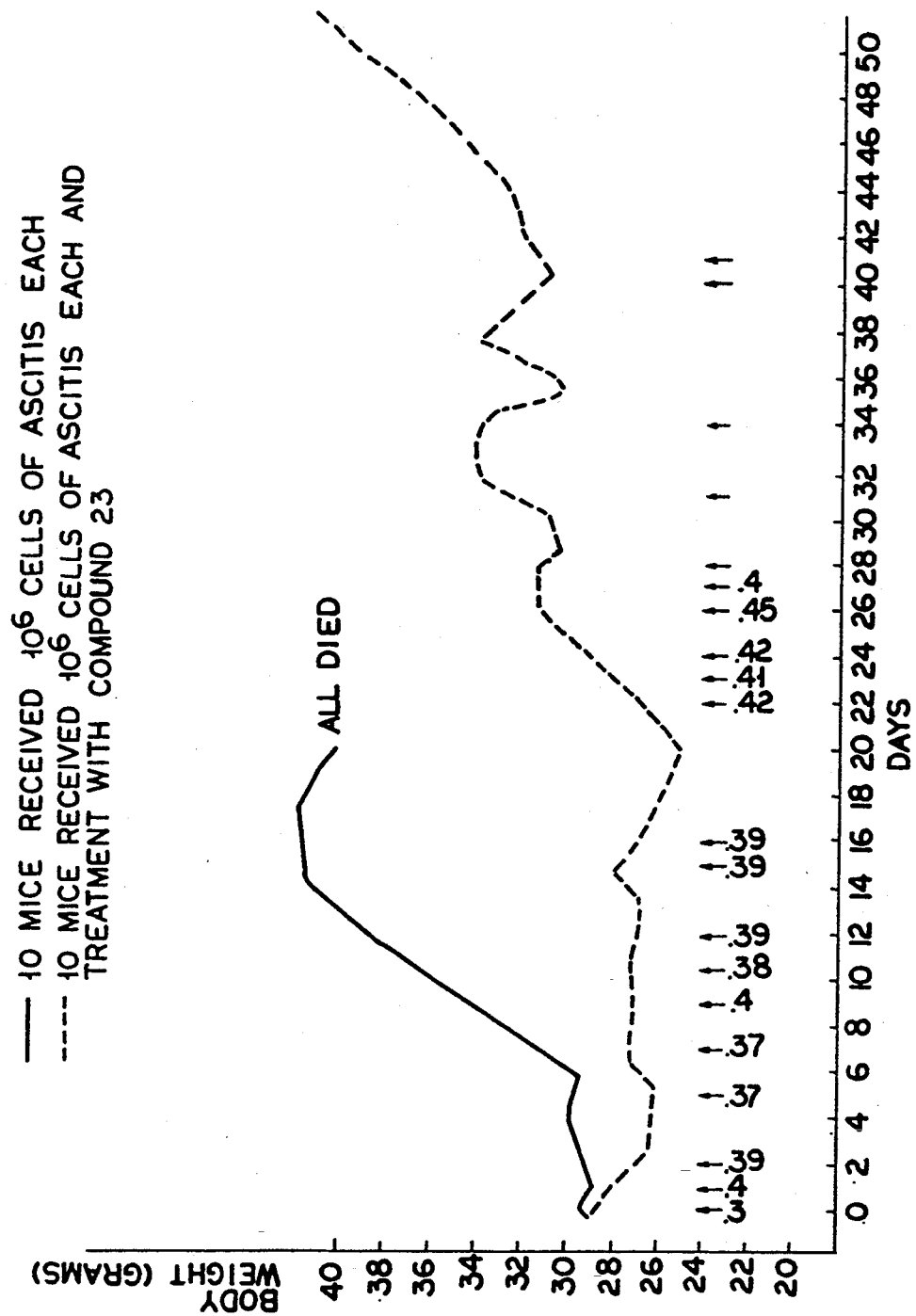

METALLO-ORGANIC COBALT COMPOUNDS AND USES THEREOF

This is a continuation of application Ser. No. 07/895,526, filed Jun. 2, 1992, now U.S. Pat. No. 5,258,403, which, in ram, is a division of application Ser. No. 07/606,070, filed Oct. 30, 1990, now U.S. Pat. No. 5,142,076, which, in turn, is a continuation of U.S. patent application Ser. No. 07/279,417, filed Dec. 2, 1988, now, U.S. Pat. No. 5,049,557 which, in turn, is a continuation-in-part of application Ser. No. 07/147,713, and application Ser. No. 07/147,714, both filed Jan. 25, 1988, now U.S. Pat. Nos. 4,866,054 and 4,866,053, respectively, which, in turn are continuation-in-parts of application Ser. No. 06/862,804, filed May 13, 1986, now abandoned.

BACKGROUND OF THE INVENTION

The present invention relates to metallo-organic cobalt compounds and their use in the treatment of subjects for inflammatory conditions, particularly arthritis, and like conditions caused by oxygen free radicals. The invention also relates to a method of treating burns and wounds and the use of the subject compounds as antimicrobial agents.

It has been recognized for some time that inflammation in mammalian species can be traced at least in part to active oxygen species, including superoxide, and radicals associated therewith at the inflammatory site. Considerable research has been undertaken to measure and detect oxygen radicals, to establish the mechanisms whereby enzymes such as superoxide dismutase are effective in countering oxygen radical toxicity, and in the development and use of copper amine oxidases in preventing tissue damage and even in promoting damage-tissue recovery. Recently superoxide dismutase, which decomposes highly toxic oxygen free radicals, has been put into veterinary use as an anti-inflammatory agent with efficacy in the treatment of conditions such as traumatic arthritis of horses.

Free radical toxicity has also been identified as operative in poisonings by various pharmacologic agents. Enzymes such as superoxide dismutase have been used as antidotes to nullify the toxic effects of the putative free radical generators in vivo.

However, the compounds which have been developed heretofore for active-oxygen or superoxide antagonism and destruction in vivo have not proven as effective as desired, or are characterized by side reactions, or cannot be made in commercially significant quantities at reasonable cost.

The present invention provides compounds and methods for the treatment of subjects having inflammatory conditions or other conditions associated with free radicals whereby the above-mentioned drawbacks are eliminated. The invention provides a method for treating a subject having a condition resulting from active oxygen or superoxide toxicity which may result in acute or chronic inflammation or other disorders, such as arthritis.

The invention also provides a method of treating burns and wounds in a subject. The treating of burns of the first, second, and third degree has long been and remains one of the most difficult medical problems. The criteria for success of any method for treating a burn includes proper contraction of the wound, epithelialization, hair follicle preservation, and the assessment of newly formed granulation tissue. Contraction represents the difference between the initial wound size of the burn and the size of the burn twelve days later (12th post burn day or PBD), which includes both open and healed areas calculated as a percentage of the initial wound size.

Epithelialization represents the percentage of the newly covered areas of the burn surface on the 12th PBD out of the total wound area on that same day. The presence of hair follicles indicates maintenance or restoration of dermal microcirculation and prevention of tissue ischemia and thus ischemic and postischemic damage. The preservation of hair follicles and their count should be carried out microscopically in tissue sections. Also important in the evaluation of medicament of treating burns is the assessment of newly formed granulation tissue. The thickness of the new collagen layer synthesized in the healing burn should be measured on PBD 12.

As part of the overall management of burn wounds, a topically antibacterial agent, such as silver sulfadiazine, may be applied. Unexpectedly, it has been found that the compounds of the present invention may be used as an antibacterial agent which can help prevent the colonization of the wound by pathologic agents. The method of the present invention maximizes epithelialization of the burn on a macroscopic level and maximizes hair follicle preservation on a microscopic level.

Additionally, it has been unexpectedly found that the compounds of the present invention cause regression in the growth of tumor cells in vivo. A method is provided for the treatment of a subject afflicted with a tumor Which comprises administering to the subject the compounds of the present invention in an amount sufficient to cause regression of the tumor cells.

SUMMARY OF THE INVENTION

The present invention provides a complex compound having the structure:

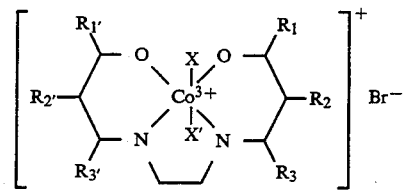

wherein $R_1$ and $R_1'$ are the same or different and each is an alkyl group, a phenyl group or a substituted derivative of a phenyl group;

wherein $R_2$ and $R_2'$ are the same or different and each is hydrogen, an unbranched alkyl group, a halide or a group having the structure

wherein R is hydrogen, an alkoxide group, an alkyl group, or OH;

wherein $R_3$ and $R_3'$ are the same or different and each is hydrogen or an alkyl group; and wherein X and X' are the same or different and each is a water soluble group having weak to intermediate ligand field strength.

The invention also provides a complex compound having the structure:

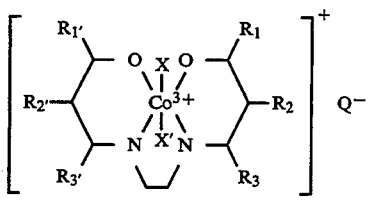

wherein $R_1$ and $R_1$, are the same or different and each is an alkyl group, a phenyl group or a substituted derivative of a phenyl group;

wherein $R_2$ and $R_2$, are the same or different and each is an unbranched alkyl, group, a halide or a group having the structure

wherein R is hydrogen, an alkoxide group, an alkyl group, or OH;

wherein $R_3$ and $R_3$, are the same or different and each is hydrogen or an alkyl group;

wherein X and X' are the same or different and each is a water soluble group having weak to intermediate ligand field strength; and Q is a soluble, pharmaceutically acceptable negative ion.

The invention also provides a method of treating a subject having a condition associated with the presence of free radicals in quantities sufficient to cause undesirable symptoms. A method of treating a wound or a burn and a method for treating a subject afflicted with tumor cells so as to cause regression of the tumor cells are also provided. The methods of the present invention involve administering to the subject (or topically administering to the burn or wound) a compound having the structure:

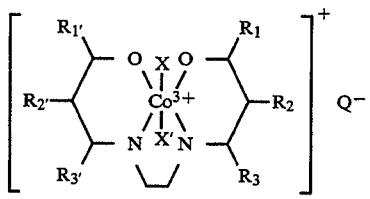

wherein $R_1$ and $R_1$, are the same or different and each is an alkyl group, a phenyl group or a substituted derivative of a phenyl group;

wherein $R_2$ and $R_2$, are the same or different and each is hydrogen, an unbranched alkyl group, a halide or a group having the structure

wherein R is hydrogen, an alkoxide group, an alkyl group, or OH;

wherein $R_3$ and $R_3$, are the same or different and each is hydrogen or an alkyl group;

wherein X and X' are the same or different and each is a water soluble group having weak to intermediate ligand field strength; and $Q^-$ is a soluble, pharmaceutically acceptable negative ion.

Furthermore the invention provides pharmaceutical compositions for the treatment of tumor cells in a subject or for the treating of undesirable symptoms associated with the presence of free radicals. The compositions comprise an effective amount of the compound and a pharmaceutically acceptable carrier. Also provided is an antimicrobial composition which comprises a suitable carrier and the compound in an amount effective to suppress the growth of microorganisms.

BRIEF DESCRIPTION OF THE FIGURES:

FIG. 2(a) and 3(a): Graph of Body Weight: vs. Days for Anti-ascites Activity of Compound 23.

DETAILED DESCRIPTION OF THE INVENTION

Figure 1A:
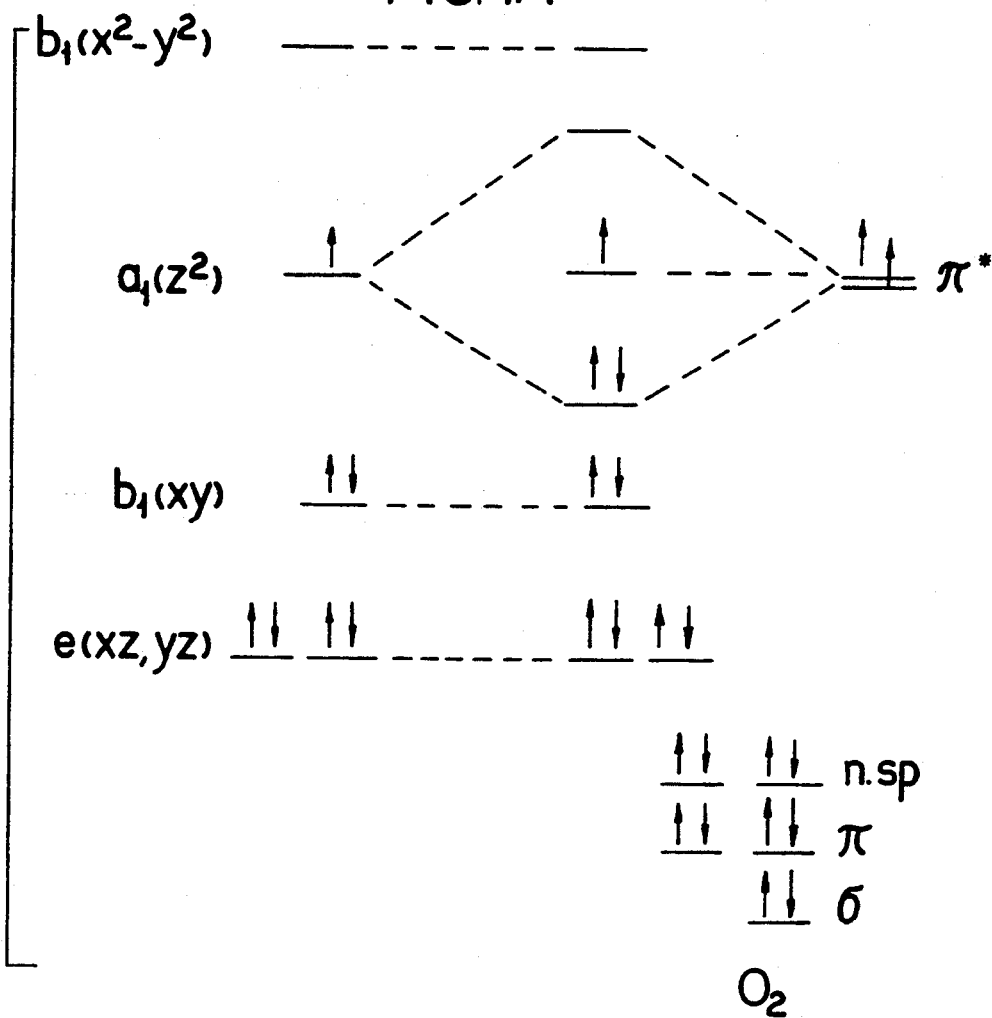
FIG. 1: A Diagram of the Molecular Orbitals for the Cobalt Complex.

The present invention provides a complex compound having the structure:

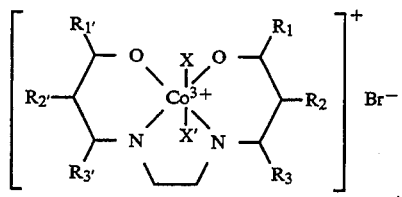

wherein $R_1$ and $R_1$, are the same or different and each is an alkyl group, a phenyl group or a substituted derivative of a phenyl group;

wherein $R_2$ and $R_2$, are the same or different and each is hydrogen, an unbranched alkyl group, a halide or a group having the structure

wherein R is hydrogen, an alkoxide group, an alkyl group, or OH;

wherein $R_3$ and $R_3$, are the same or different and each is hydrogen or an alkyl group; and wherein X and X' are the same or different and each is a water soluble group having weak to intermediate ligand field strength.

Also provided is a complex compound having the structure:

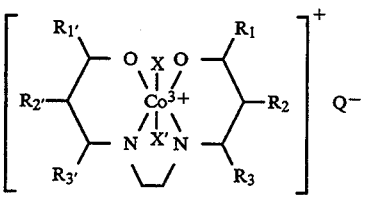

wherein $R_1$ and $R_1$, are the same or different and each is an alkyl group, a phenyl group or a substituted derivative of a phenyl group;

wherein $R_2$ and $R_2$, are the same or different and each is an unbranched alkyl group, a halide or a group having the structure

wherein R is hydrogen, an alkoxide group, an alkyl group, or OH;

wherein $R_3$ and $R_3$, are the same or different and each is hydrogen or alkyl group;

wherein X and X' are the same or different and each is a water soluble group having weak to intermediate ligand field strength; and Q is a soluble, pharmaceutically acceptable negative ion.

The compounds of the present invention may be crystallized with numerous counteranions. Those which are pharmaceutically acceptable and are water soluble, such as halide ions, $PF_6^-$ and $BF_4^-$, are preferred. The bromine salts of the present compounds are the most preferred because they are the easiest to crystallize and are more water soluble than other salts of the compounds.

As discussed above the $R_1$ and $R_1$, groups of the compound may be the same or different from each other and each may be an alkyl group, a phenyl group or a substituted derivative of a phenyl group. Preferably the alkyl group is a $C_1$-$C_5$ group with methyl, ethyl and butyl groups being particularly preferred. Suitable substituted derivatives of the phenyl group are derivatives wherein each substituent is a halide, an alkyl group or a group having the structure

where R is hydrogen, an alkoxide group, an alkyl group or an OH group. To date the most useful derivatives have proven to be those in which the substituents are halides, carbonyl groups or alkyl groups.

The $R_2$ and $R_2$, groups of the complex compounds of the present invention may also be the same or different and may be hydrogen, an unbranched alkyl group, a halide or a group having the structure

where R is hydrogen, an alkoxide group, an alkyl group or an OH group. In certain embodiments, it is preferred that $R_2$ and $R_2$, are chlorine or hydrogen atoms or a $C_1$-$C_3$ alkyl group. In embodiments where $R_2$ has a structure

it is preferred that R is hydrogen, a methyl group or an OH group.

The $R_3$ and $R_3$, of the complex compounds of the present invention are the same or different and each may be hydrogen or an alkyl group, preferably a $C_1$-$C_3$ alkyl group.

With respect to the X and X' groups, it is preferred that these groups are water-soluble and have a weak to intermediate ligand field strength. Ligands are arranged in a spectrochemical series according to the magnitude of their field strength or the "$\Delta_0$" they bring about. The symbol $\Delta_0$ represents the difference between the energies of the $d_{xy}$, $d_{xz}$, and $d_{yz}$ orbitals and the $d_z^2$ and $d_{x^2-y^2}$ orbitals. From experimental studies, it is known that the order of ligands, based on their ligand field strength, is approximately the same for the complexes of all the transition metals in their common oxidation states with only an occasional inversion of order between ligands that stand near to one another. A typical order of some common ligands is as follows:

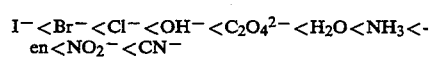

The cyanide ion, which stands at the opposite end of the series from the hellions, has the strongest ligand field strength and induces the largest d-orbital splitting of any ligand listed. On the other hand, the halide ions such as $Br^-$ and $Cl^-$ have weak ligand field strength and induces the smallest d-orbital splitting. Ligands such as $NH_3$ and $OH^-$ have-intermediate ligand field strength. For general background information, see F. Albert Cotton and Geoffrey Wilkinson, "Advanced Inorganic Chemistry", John Wiley & Sons 4th ed, p. 663. In the present invention,it is preferred that X and X' are ligands with weak to intermediate ligand field strength, such as halides or $NH_3$, $H_2O$, or dimethyl sulfoxide.

Particular preferred embodiments of the complex compounds of the present invention are as follows:

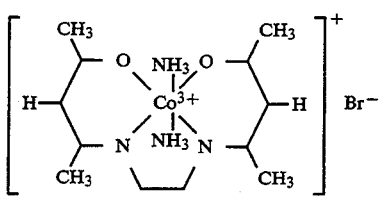

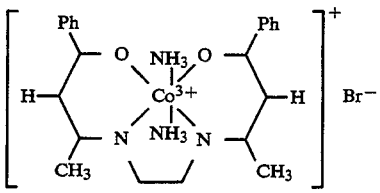

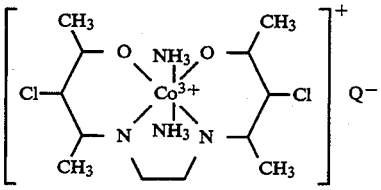

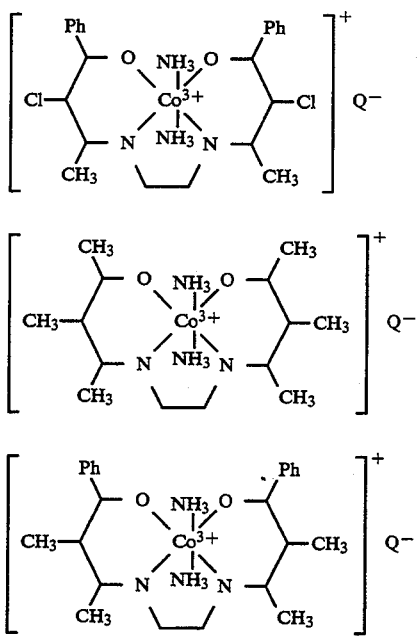

wherein Ph is a phenyl group,

The invention also provides a pharmaceutical composition and method for treating a subject having a condition associated with the presence of free radicals in quantities sufficient to cause undesirable symptoms, The pharmaceutical composition comprises a pharmaceutically acceptable carrier and the compound of the present invention in an amount effective to alleviate the undesirable symptoms associated with the presence of the free radicals. The method comprises administering to the subject the compound in an amount effective to alleviate the undesirable symptoms.

The method may be used for the treatment of any condition associated with free radicals. It is however most effective against conditions associated with oxygen free radicals, such as $O_2^-$. Such conditions may comprise inflammation, including synovial inflammation and arthritis, ulcers such as diabetic ulcers, and conditions caused by the loss of circulation due to free radicals, such as hair loss due to the loss of dermal microcirculation.

Preferably, the method is used in the treatment of acute or chronic arthritis with a dosage of the compounds of 0.1 to 250 mg/kg (especially about 1 to about 200 mg/kg) of body weight, but in all cases at most 50% of the $LD_{50}$ value of the compound, when the compound is administered orally as is preferred. However, the complex compound or a combination of the complexes can be administered subcutaneously or even topically in a suitable vehicle, e.g. physiological saline in the case of s.c. administration and dimethylsulfoxide (DMSO) in the case of a topical administration, although ointments, salves or like conventional vehicles may be employed.

For oral administration, the complex or mixture of complexes may be prepared in suitable dosage forms. For example it may be prepared as dragees, as capsules, as tablets, as an elixir or other oral dosage form.

The dose may be administered one to six times daily, depending upon the severity of the inflammatory condition, preferably under medical supervision so that the dosage can be reduced or the number of daily administrations limited as the inflammatory condition subsides.

The compounds of the invention may also have prophylactic properties in preventing the spread of arthritic inflammation and have been found to be effective in reducing the severity of the actual condition which develops in subjects who are prone to such inflammatory states. The compounds may also be effective in preventing postischemic heart damage and for geriatric applications other than antiarthritics.

It is also contemplated that the compounds of the invention may be used in conjunction with known anti-inflammatory agents with propionic acid side chains, especially indomethacine, to further alleviate the suffering of arthritic inflammation.

The invention also provides an antimicrobial composition which comprises a suitable carrier and the compound of the present invention in an amount effective to suppress the growth of microorganisms. The antimicrobial composition or compounds of the present invention may be used for the treatment of a wound or burn by topically administering to the wound or burn the composition or compounds. The compounds may also be used in the treatment of conditions which are normally treated with antimicrobial or antibacterial agents. For example, the compounds may be used in the topically treatment of an infectious disease or an abrasion as an antibiotic.

The cobalt complexes of the present invention are water-soluble and may be dissolved in a number of carriers. Suitable carriers include polar, protic solvents such as water or especially normal saline. The cobalt complexes may also be suspended in a suspension medium that is not miscible with water, for example petrolatum.

The concentration of the complexes in the solvent or suspension medium can vary from 0.1 to 50 mg/ml. A preferred concentration range lies between 1 and 10 mg/ml.

The complexes may be applied to the site of the burn, wound, abrasion, etc. in the form of an aerosol, in the form of a salve, ointment, or cream, or directly in a liquid solvent, preferably normal saline, by the use of a medicine dropper. Furthermore the complexes may be applied to the burn site together with a topical anaesthetic agent such as benzocaine, a soothing agent such as menthol, an antibacterial agent such as bacitracin, or a combination of these ingredients.

The method is particularly effective for killing microorganisms such as *Strep. β hemolytic*, *Strep. α hemolytic*, Enterococci, *Staph. coagulase* (+), *Staph. coagulase* (−), *E. Coli*, Klebsiella, Pseudomonas, Proteus, or *C. albicans*.

It has also been-found that the compounds of the present invention are effective in the treatment of subjects having tumors. Administration of the compounds to a subject afflicted with tumor cells causes a regression in the growth of the tumor cells. The compound may be directly administered to the subject or it may be administered in a pharmaceutical composition which comprises an e effective anti-tumor amount of the compound and a pharmaceutically acceptable carrier. This method has been found to be particularly effective in the treatment of tumors associated with ascites cells.

It is also contemplated that the compounds and compositions of the present invention may be used in the treatment of other conditions associated with free radicals, such as poisonings with pharmacologic agents or conditions caused by ionizing radiation. The compounds may also be used in industrial applications where free radicals, such as oxygen radicals, are undesirable; for example, in wastewater treatment as an oxygen scavenger.

Other embodiments and uses for the compounds of the present invention will become apparent to those skilled in the art upon a reading of the present disclosure. These uses and embodiments are intended to be within the spirit and scope of the present invention.

The invention is further illustrated in the Experimental Details section which follows. This section is set forth to aid in an understanding of the invention but is not intended to, and should not be construed to, limit in any way the invention as set forth in the claims which follow thereafter.

EXPERIMENT DETAILS

I. Synthesis:

Several cobalt(III) complex compounds having the general formula [CoL(NH$_3$)$_2$]$^+$, wherein L represents a tetradentate ligand with two oxygen and two nitrogen donor atoms, have been prepared and characterized. The purity of the compounds was established by elemental analysis, N.M.R. and U.V.-visible spectroscopy. The geometry around the cobalt atom was established by X-ray crystallography. Analytical reagent grade chemicals were used without further purification. A detailed description for a typical preparation for each of the compounds follows. Of the compounds described only [Co(L23) (NH$_3$)$_2$]$^+$ have been reported previously[1].

1. Synthesis of [CoL23(NH$_3$)$_2$]Cl, (L23=N,N'-bis(acetylacetone)ethylenediimine)

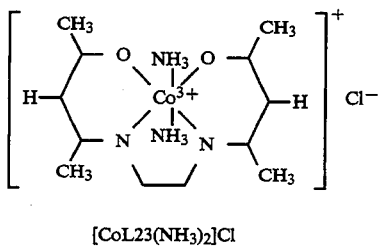

[CoL23(NH$_3$)$_2$]Cl

The tetradentate ligand was prepared as described by McCarthy[2]. To 0.023 moles of L23 dissolved in 100 ml of methanol was added 0.016 moles of COCl$_2$H$_2$O dissolved in 100 ml of methanol. Concentrated NH$_4$OH was added dropwise with continuous stirring until the pH became basic (pH=8). Stirring was continued for an additional three hours. The resulting precipitate was filtered and recrystallized from hot ethanol/water.

Found; C, 40.9%; H. 6.75%; N, 16.1%. Calculated for C$_{12}$H$_{24}$O$_2$N$_4$CoCl; C, 41.09%; H, 6.90%; N, 15.9%. MW=350.4.

2. Synthesis of [Co(L64)(NH$_3$)$_2$]Cl, (L64=N, N'-bis(benzoylacetoneethylenediimine).

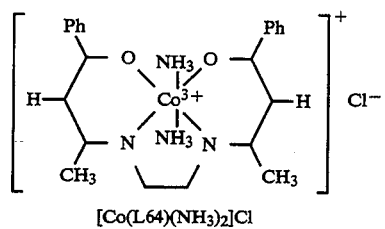

[Co(L64)(NH$_3$)$_2$]Cl

L64 was prepared as described by McCarthy[2]. To 0.022 moles of L64 dissolved in 100 ml of CH$_2$Cl$_2$ was added a filtered solution of 0.020 moles of CoCl$_2$6H$_2$O in 100 ml of absolute methanol. A concentrated solution of NH$_4$OH was added slowly with continuous stirring until the solution became basic (pH=8). Stirring continued for an additional 4 hrs. The solution was concentrated to a volume of 50 ml and filtered. Slow evaporation of the mother liquor gave the desired product.

Calculated for C$_{22}$H$_{28}$O$_2$N$_4$CoCl.H$_2$O: C, 54.72%; H, 6.20%; N, 11.61%; Found: C, 54.61%; H, 6.05%; N, 11.49%. MW=482.4

3. Synthesis of [Co(L67)(NH$_3$)$_2$]Cl, (L67=N,N'-bis(chloroacetylacetone)ethylenediimine)

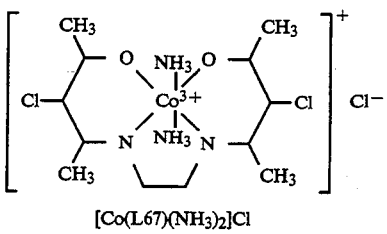

[Co(L67)(NH$_3$)$_2$]Cl

L67 was prepared as previously described[3]. [Co(L67)(NH$_3$)$_2$]Cl was prepared by the same procedure as [C0L23)(NH$_3$)$_2$]Cl. Found; C, 34.61%; H, 5.38%; N, 13.03%. Calculated for C$_{12}$H$_{22}$O$_2$N$_4$CoCl$_3$; C, 34.35%; H, 5.02%; N, 13.35%. MW=419.32

4. Synthesis of [Co(L68)(NH$_3$)$_2$Br, (L68=N,N'-bis(chlorobenzoylacetone)ethylenediimine)

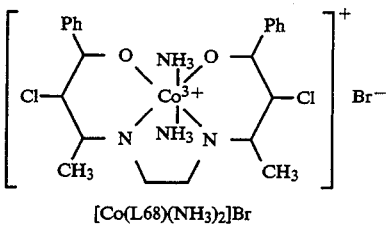

[Co(L68)(NH$_3$)$_2$]Br

L68 was prepared by direct chlorination of L64 with a slight excess of N-chlorosuccinimide (NClS)[4] · 0.1 moles of L64 was dissolved in 700 ml of ice cold CH$_2$CL$_2$. 0.25 moles of NC1S was added and the reaction stirred for 20 min. The ligand precipitated as a yellow powder which was filtered, washed with ether and dried. 0.005 moles of L68 was suspended in 100 ml of absolute ethanol under nitrogen to which 0.01 moles of KOH dissolved in 25 ml of methanol was added. 0.0045 moles of Co(OAc)$_2$.4H2O in 25 ml of methanol was slowly added to the above suspension with continuous stirring. The reaction mixture was heated to 50° C. for 1 hr. After cooling, the orange precipitate of

[Co(L68)] was filtered, washed with ethanol and dried. 0.002 moles of the Co(II) complex [CoL68] was suspended in 100 ml of methanol under $N_2$. 1 ml of 30% $H_2O_2$ was added dropwise and anhydrous ammonia was bubbled through the reaction mixture until all the Co(II) complex had been dissolved. At this point, bubbling of $N_2$ was discontinued and the solution was stirred for an additional 1 hr. The solution was, filtered and three equivalents of NaBr dissolved in a minimum amount of water was added. Slow evaporation of the solution yielded the desired product.

Found: C, 43.44%; H, 4.46%; N, 9.07%. Calculated for $C_{22}H_{26}BrCl_2N_4O_2Co \cdot H_2O$: C, 43.58%; H, 4.65%; N, 9.24%. MW=605.78

5. Synthesis of [Co(L69) (NH3)2]Cl. (L69=N.N'-bis(-methylacetylacetone)ethylenediimine)

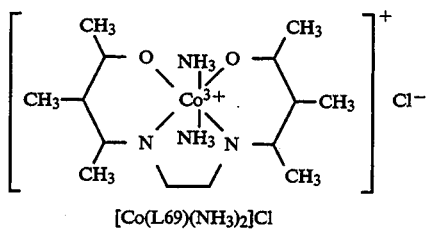

[Co(L69)(NH3)2]Cl

L69 was prepared by condensation of anhydrous ethylenediamine with methylacetylacetone[5]. The complex is prepared by the same procedure as described for [Co(L23)(NH3)2]Cl.

Calculated for $C_{14}H_{28}N_4O_2CoCl \cdot H_2O$; C, 42.42%, H, 7.57, N, 14,14%. Found: C, 42.14%; H, 7.48%; N, 14.01%. MW=396.4

6. Synthesis of [Co(L70)(NH3)2]Br, (L70=N,N'-bis(-methylbenzoylacetone)ethylenediimine)

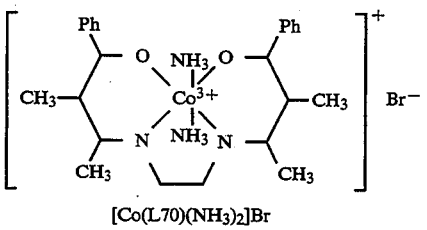

[Co(L70)(NH3)2]Br

L70 was prepared by condensation of ethylene diamine with methylbenzoylacetone[6]. The Co(III) complex was prepared via the Co(II) complex by the procedure described for [Co(L68)NH3)2]+.

Found: C, 46.87%; H, 5.03%; N, 8.95%. Calculated for $C_{24}H_{32}B_1 \cdot N_4O_2$ Co:47.07H, 5.27%; H, 5.27%; N,, 9.15%, MW=611.9

All complexes described can be crystallized with other counteranions. Those anions which give the best solubility in water here chosen here.

The reaction of Co(II) complexes with molecular oxygen has been studied extensively[7,8]. Normally, cobalt(II) forms 2:1 peroxo bridged complexes in aqueous solutions[8]. In recent years, a number of Co(II) complexes have been reported to give 1:1 cobalt-oxygen adducts at room temperature. These complexes usually contain ligands which when bound to Co(II) give rise to a low spin planar geometry. Addition of base and $O_2$ to these complexes leads to the formation of octahedral complexes where the base and the $O_2$ occupy axial positions[9].

Figure 1B:
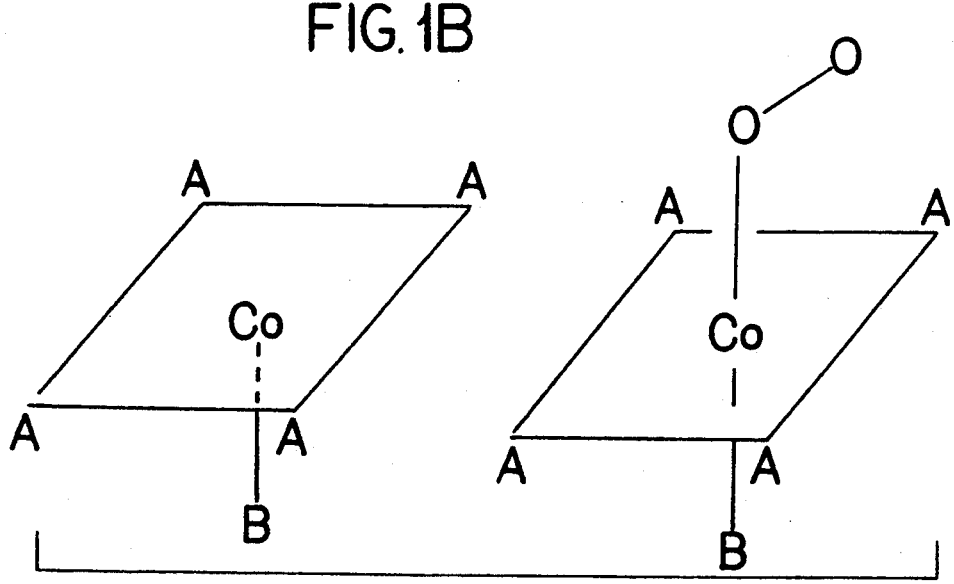

On the basis of measurements utilizing a variety of physical techniques it is now a well accepted fact that the most accurate electronic structure description for the Co:$O_2$ moiety is a Co,(III) ion bound to $O_2^-$, where the actual amount of Co→>$O_2$ electron transfer depends on the nature of the ligand and the donor set [9,10]. It has been shown that electron transfer increases with increase of the ligand field strength[7]. This can be easily understood from the molecular orbital diagram depicted in FIG. 1. In FIG. 1, the donor atoms A define the basal plane of the molecule, while B represents the; axial ligands. As the ligand field strength of the donor atoms around the cobalt increases, the metal orbitals (especially $d_z^2$ and $d^2-y^2$ which are $\sigma$ orbitals) are raised in energy relative to the $\pi$ orbitals of $O_2$ and more electronic charge is trans feted from the metal to the bound dioxygen, i.e., the $O_2$ molecule attains more Ohd 2− character. Thus, considering electronic structural arguments only, one can conclude that a Co(III) complex with a set of six donor atoms (four A donors, and two B donors) having an intermediate ligand field strength could be effective in reacting with $O_2^-$ by either forming a stable Co(III)-$O_2$ adduct (the $O_2$ substitutes one of the B ligands), or by oxidizing $O_2^-$, liberating dioxygen and yielding a Co(II) complex. The relative strength of the different ligands is well known from the spectrochemical series. However, it should be quite clear that a sterically unstrained ligand system which can easily accomodate both metal oxidation states [Co(II), Co(III)] with minimal reorganization of the geometry around the: metal and which does not lead to a high spin Co(II) complex should facilitate the reaction.

Thus, on the basis of geometrical, steric and electronic requirements we suggest that a Co(III) complex having a quadridentate ligand which imposes planarity on the. octahendral basal plane should be a suitable candidate for reaction with the $O_2^-$ radical anion. The effectiveness of this reaction will depend on the nature of the quadridentate ligand, its ligand field strength and on the nature of the axial ligands B.

The complexes [CoL(NH3)2]+ fit nicely with the set of requirements given above. First, the six donor atoms $N_4O_2$ give rise to an intermediate ligand field. Secondly, the quadridentate ligand L when bound to Co(III) gives rise to a 6,5,6 ring system where the six membered rings are unsaturated, thereby ensuring the planarity of the complex basal plane without steric strain, as has been determined from X-ray crystal structure analysis. Thirdly, the ligand L when bound to Co(II), gives a low spin, planar complex.

It should be pointed out that the unsaturation of the six-membered rings is important not only because it ensures the required geometry, but also because it provides for an effective pathway for transmitting electronic effects of different substituents to the cobalt center, thereby affecting the relative energies of the metal d orbitals.

II. In vivo Inflammatory Studies:

The drugs used are prepared just before performing the experiment. Drugs are dissolved at a concentration of $10^{-2}M$ (or $2 \times 10^{-2}M$ or $4 \times 10^{-2}M$) in pyrogen free sterile saline. The dissolved drug is then filtered through a sterile and pyrogen-free 0.2 micron filter (Acrodisc, Gelman).

Procedure 8-12 CD-1 female mice (Charles River), age 2-5 months are numbered, weighed and distributed to 2-3 cages, 3-4 mice in each cage. 0.2 ml of pyrogen-free saline or drug are injected subcutaneously in a randomized order.

Thirty minutes after injecting the drugs or the saline, the right paw of each mouse is injected with 25 microliters of 1% carrageenin (viscarin type, Marine Colloids) in pyrogen-free saline or with 5 microliters (0.227 U) of xanthineoxidase (Sigma).

1.5 hr to 2 hrs after injecting the inflammatory stimulus to the right paw, both paws of the animal are amputated at the knee joint and weighed. The uninjected left paw serves as an internal control for the degree of swelling of the right paw in each animal.

In some experiments the surface temperature of the right and left paws were recorded also before the amputation was performed.

Calculations

The difference in mg between the weight of the right and left paw in control animals (injected with saline) represents 100% of the acute inflammatory response. Concomitantly, the difference between paws of the drug treated animals is calculated and compared to control. Results for $[CoL23(NH_3)_2]Cl$ (designated as "23" in tables) are shown in Tables 1, 2 and 3 which follows.

TABLE 1

Effect of several products on carrageenin paw oedema in mice measured by paw weight.

| Product | No. of expts. | total mice | route of admin. | average mg/kg | Paw Weight % activity | % inhibition |
|---|---|---|---|---|---|---|
| saline | — | — | *S.C. | — | 100% | 0 |
| 3 | 4 | 14 | *S.C. | 25 | 63.1% | 36.9% |

TABLE 2

Effect of several products on xanthine-oxidase paw oedema measured by temperature reduction

| Product | No. of expts. | total mice | route of admin. | average mg/kg | % activity | % inhibition |
|---|---|---|---|---|---|---|
| saline | — | — | *S.C. | — | 100% | 0 |
| 23 | 2 | 6 | *S.C. | 22.7 | 31% | 69% |

TABLE 3

$LD_{50}$ and $ED_{50}$ of various drugs on xanthine oxidase and carrageenin paw oedema in mice

| Drug | $LD_{50}$ mg/kg | stimulus :xanthine oxidase measurement :temp. $ED_{50}$ mg/kg | carrageenin measurement weight mg $ED_{50}$ mg/kg |
|---|---|---|---|
| 23 | 75 | <38 | 25 |

Compound 64 ($[Co(L64)(NH_3)_2]Cl$) was found to be as effective as or more effective than compound 23 in corresponding tests. Both compounds were found to be effective in reducing oedema upon oral administration in force feeding with pills containing 8 mg of active ingredient and administered in a quantity sufficient to provide an effective dose. The pills were enterally coated (see below).

Example 1

The composition of tablets is as follows:

| active ingredient (one or both of compounds 23 or 64 | 25.0 mg. |
|---|---|
| corn starch | 97.0 mg. |
| polyvinyl pyrrolidone | 175.0 mg. |
| magnesium stearate | 3.0 mg. |
| | 300.0 mg. |

The active ingredient and the corn starch are wetted by an aqueous polyvinyl pyrrolidone solution of approx. 15% w/v, followed by granulation, and drying of the wet granules at about 40°–45° C. The dried granulate is thoroughly mixed with magnesium stearate, and the mixture so obtained is further processed by a tablet machine, equipped with an appropriate pressing tool, to give tablets of 300 mg. weight containing 25 mg. of active ingredient. One manufacturing lot includes 100 tablets.

Example 2

Dragees of the following composition are prepared:

| active ingredient (one or both of compounds 23 or 64) | 50.0 mg. |
|---|---|
| lactose | 94.0 mg. |
| polyvinyl pyrrolidone | 4.0 mg. |
| magnesium stearate | 2.0 mg. |
| | 150.0 mg. |

Granulates are prepared according to Example 1, and from them dragee kernels of 150 mg. weight are pressed. The dragee kernels are coated with a layer containing sugar and talc followed by coloring with an approved food colorant and polishing with beeswax.

Example 3

25 mg. of active ingredient (one or both of compounds 23 or 64) are dissolved in 100 ml. of distilled water. The solution is filled into 500 ampules. In this way ampules containing 2 ml. of a solution containing 25 mg./ml. of active agent each are obtained. The contents of an ampule are injected subcutaneously.

Example 4

Gelatin capsules of the following composition are prepared:

| active ingredient (one or both of compounds 23 or 64) | 25.0 mg. |
|---|---|
| maize starch | 122.0 mg. |
| colloidal silica | 3.0 mg. |
| | 150.0 0 mg. |

The ingredients are homogenized, and the homogenate is put into hard gelatine capsules. 1000 capsules of 150 mg. (filling) weight each, containing 25.0 mg. of active ingredient per capsule, make a lot.

Example 5

Pills of the active ingredient are enterally coated with a melt of 45 parts of n-butyl stearate, 30 parts of carnauba wax and 25 parts of stearic acid, all by weight, at a temperature of 75° C.

II. Superoxide Scavenging

Compounds 67, 68, and 69 ([Co(L67)(NH3)2]Cl; [Co(L68)(NH3)2]Br; [Co(L69)(NH3)2]Cl, respectively) were tested spectrophtmerically for $O_2$ quenching (reduction of NBT in the presence of xanthine and xanthine oxidase as the generating system of superoxide radicals). These compounds were also evaluated by quenching of $O_2$ produced by macrophages in tissue culture. Macrophages are a source of superoxide radicals in inflammatory states.

The activity of these compounds were assessed and compared to compounds 23 and 64 Which hereinabove are reported to be effective superoxide radical scavengers and effective in the treatment of rat adjuvant arthritis. Subsequently, these two compounds were also found to be effective in burn wound healing. Table 4 summarizes the results obtained with compounds 67, 68, 69 as compared with 23 and 64.

As depicted in Table 4 compounds 23 and 67 have given similar results both in the test tube and with macrophages.

50% $O_2^-$ scavenging was achieved at a concentration of about $10^{-5}$M whereas Compounds 64 and 68 gave diverse results with the two methods: in the test tube the compounds were very effective, yielding 50% $O_{-2}$ quenching at concentrations of $2-8\times10^{-6}$M whereas in the macrophage system there was a decrease in superoxide scavenging ability to the range of $10^{-4}$M. Compound 69 was not as effective in $O_2$ scavenging as judged by either method. BSA was used as a chelating agent, in order to determine the stability of each ligand with the metal in physiological fluids. Compound efficacy in the presence of BSA was as follows: 23>67>69>64.

TABLE 4

The drug concentration [M] at which 50% superoxide quenching is achieved, as measured by spectrophotometric and tissue culture methods. Also, the concentration of the drug at which 50% of protein synthesis is inhibited in cultured macrophages.

| Compound # | Test tube determination(a) | Macrophages −BSA(b) | +BSA(c) | 50% inhibition of protein synthesis(d) |
|---|---|---|---|---|
| 23 | $7.7 \pm 0.5 \times 10^{-5}$ | $7.0 \pm 0.8 \times 10^{-5}$ | $1 \times 10^{-4}$ | $6.0 \times 10^{-5}$ |
| 64 | $8.0 \pm 0.64 \times 10^{-6}$ | $1.4 \pm 0.23 \times 10^{-4}$ | $6 \times 10^{-4}$ | $6.4 \times 10^{-5}$ |
| 67 | $7.4 \pm 0.9 \times 10^{-5}$ | $5.5 \pm 0.5 \times 10^{-5}$ | $2 \times 10^{-4}$ | $6.5 \times 10^{-5}$ |
| 68 | $2.6 \pm 0.2 \times 10^{-4}$ | $2.0 \pm 0.2 \times 10^{-4}$ | not tested | $1.0 \times 10^{-4}$ |
| 69 | $5.0 \pm 0.04 \times 10^{-4}$ | $3.7 \pm 0.7 \times 10^{-4}$ | $3 \times 10^{-4}$ | $6.0 \times 10^{-5}$ |

Table 4 gives the comparative activity of each compound as determined by various methods of measuring superoxide scavenging. The values represent the concentration of each compound at which 50% superoxide inhibition was achieved ±SEM. These are the averages of 3 experiments each done in duplicate.
(a) xanthine-xanthine oxidase system.
(b) and (c) macrophage system, without or in the presence of .15% BSA as a chelating agent, respectively.
(d) Drug concentration at which 50% of protein synthesis in the cells is inhibited.

Figure 2A:
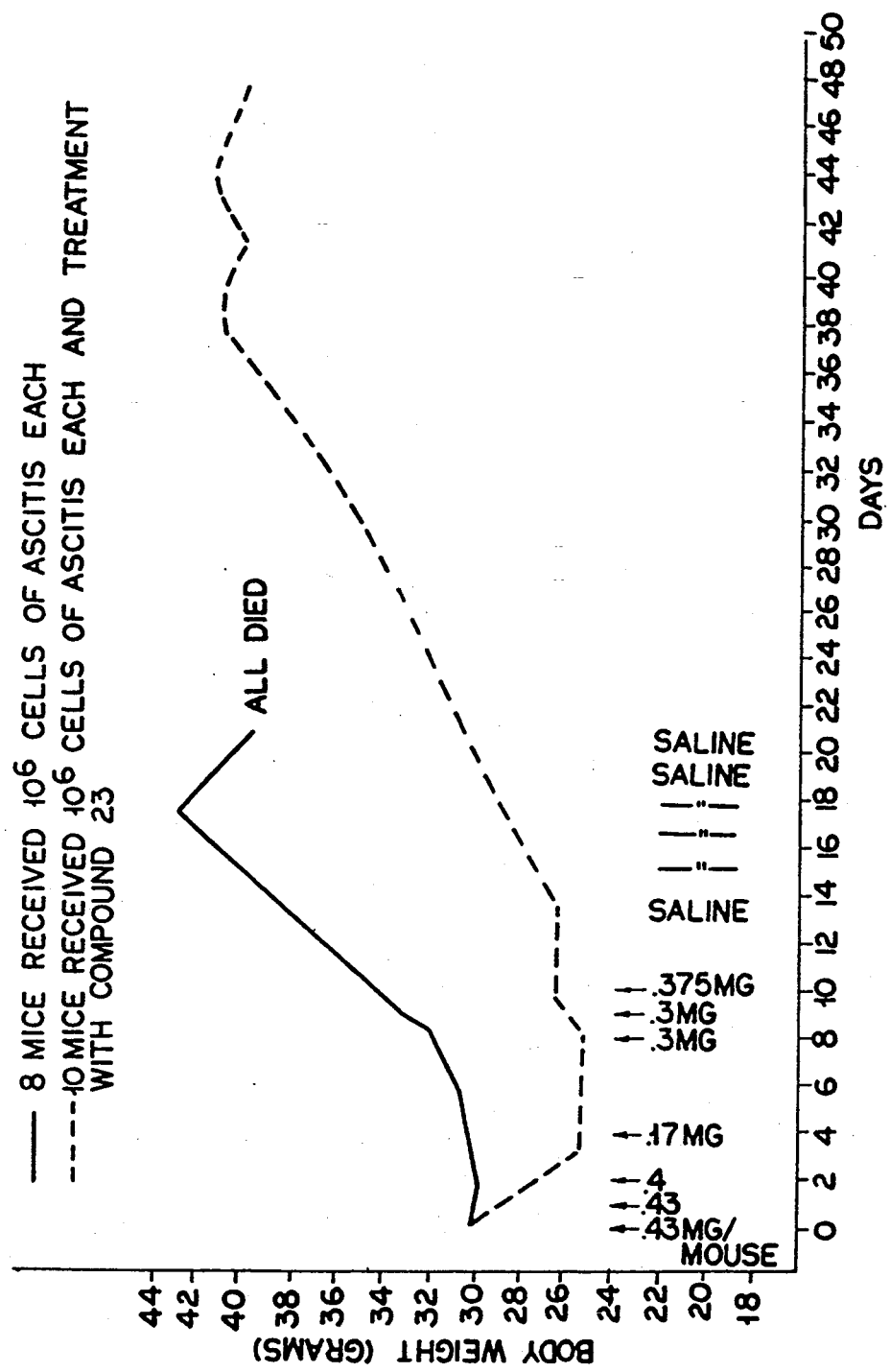
Figure 2B:
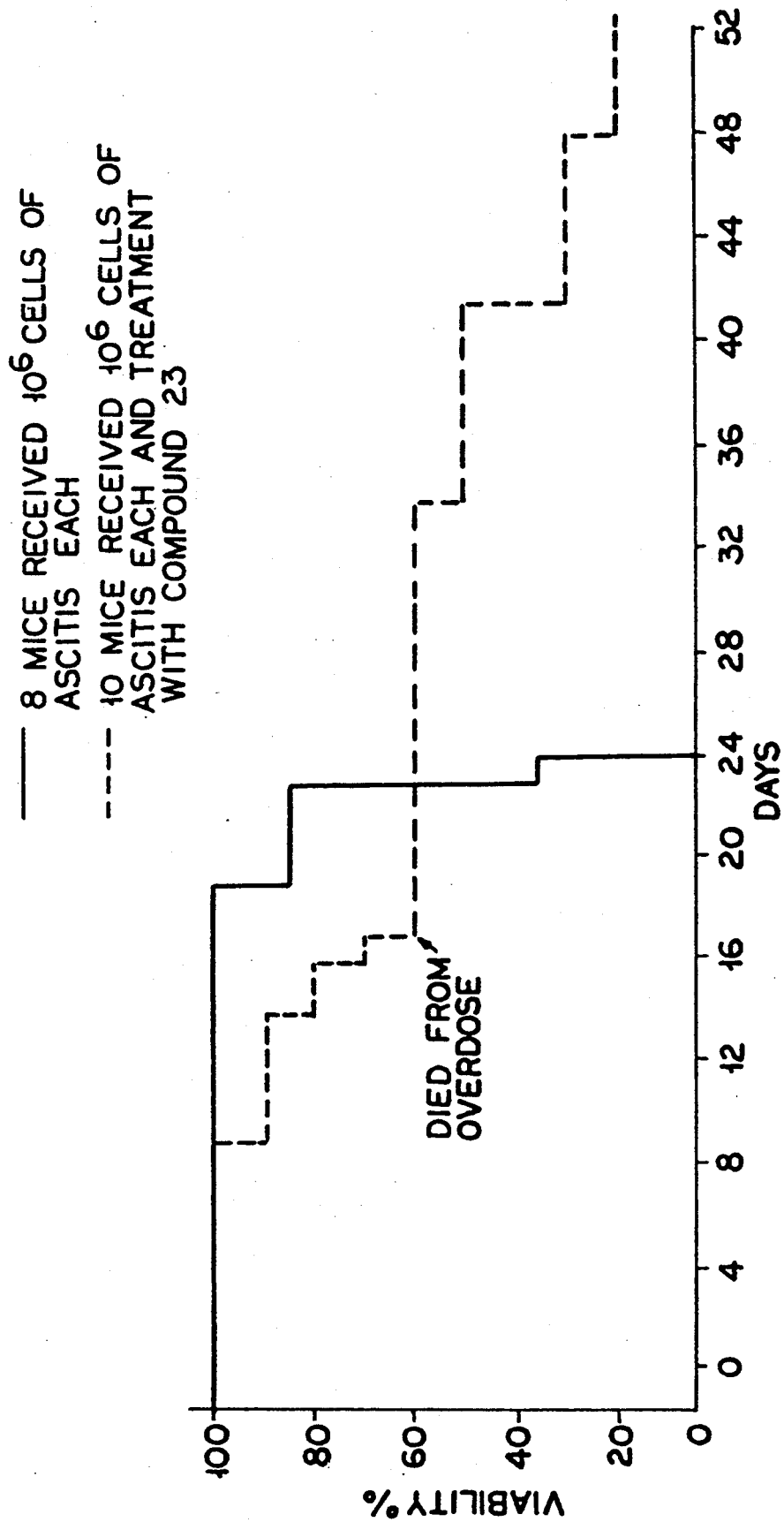
FIG. 2(b) and 3(b): Graph of % Viability vs. Days for Anti-ascites Activity of Compound 23.
Figure 3B:
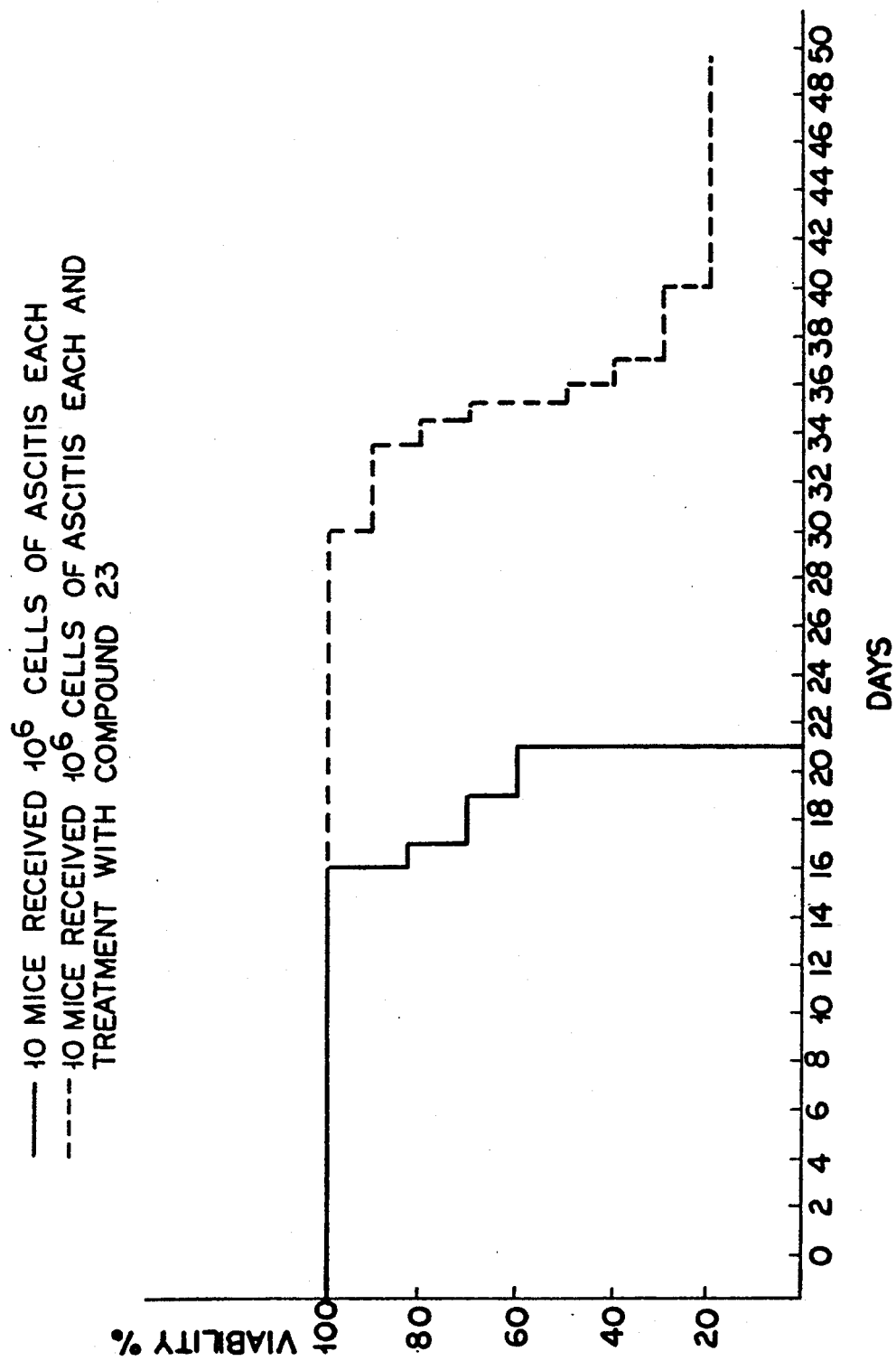

III. Anti-ascites (tumor) activity of compound 23:

The effect of compound 23 on ascites tumor development in C57/B1 mice was tested. Each mouse was injected intraperitoneally with either $5\times10^5$ or $1\times10^6$ Ehrlich ascites cells. Half of the mice received injections of 12-16 mg/kg of compound 23 and half remained untreated. Body weight and survival were tested at the time intervals indicated in FIGS. 2 and 3. The results of two (out of seven) representative experiments are depicted in FIGS. 2 and 3. The main conclusions so far are: a) the compound inhibits tumor proliferation and delays mortality caused by the tumor very considerably; b) experiments with doses (toxicity) and intervals between injections are needed; and c) the results are encouraging because the amount of tumor cells injected is very high and kills 100% of the animals within 20-21 days.

IV. Burn/wound healing for Compounds 23 and 67:

Female and male Hartley derived albino guinea-pigs were used throughout this study. They were housed individually and fed ad libitum normal guinea-pig's chow and water, supplemented with 1 gm of Vitamin C per week.

The back of each animal was clipped and depilated 24 hours prior to the burn injury. Two symmetrical mirror-image round burns were inflicted on the back of each animal with an aluminum template heated to 75° C. and applied for 5 seconds under general anaesthesia (ketamine 150 mg/kg I.M.). Intraortic india ink injection indicated in our preliminary studies that the injuries were deep second-degree burns. The burn areas were dressed in the same fashion as is routinely done in cases of such burns.

Application of the compounds for Experiments 3, 4 and 5 was carried out as follows: five times a day for the first four days and twice daily from the fifth to the 12th day. On day twelve the animals were sacrificed and the wound tissues were sent for histological examination.

Control wounds were treated with 1 mg bovine serum albumin/1 ml saline or with 1 ml of saline only. Catalase treatment was also applied in 1 mg/ml saline. Compound 23 was applied at either 3 mg/ml or varying concentrations of 3 mg/ml for the first four days, 2 mg/ml twice daily from the 5th to the 8th day and 1 mg/ml twice daily from the 9th to the 12th day.

The wounds were selected for treatment at random. Three or four treatment groups were performed in each experiment. All dressings were changed under general anaesthesia every four days, at which time wound tracing for healing analysis was performed.

The evaluation of healing is based upon the following four criteria:

1. Epithelialization—wound epithelialization expressed as percent was calculated employing the following formula:

$$E_1 = \frac{A12 - Ao}{A12} \times 100$$

where
$E_1$ = rate of epithelialization expressed in percent.
A12total = wound size on the: 12th day post burn both opened and healed wound.
Ao = area of open wound on the same 12th day.
E1 represents the % of the newly covered area out of the total wound area on the 12th day. E2 represents the % of the healed area on the 12th day out of the total area of the primary wound induced at zero time.

2. Contraction—The burn wound size as delineated by its outer boundaries was traced on a transparent polyethylene sheet on post burn days (PBD) 4, 8 and 12. Areas were measured by a system composed of an IBM PC computerized video-camera interfaced with a specially designed software. The percentage of contraction was calculated according to the following formula:

$$C = \frac{A_1 - A_{12}}{A_1} \times 100$$

where:

C—percentage of contraction on PBD 12.
$A_1$—initial burn wound size.
$A_{12}$—burn wound size PBD 12 (opened and healed wound.

Excessive contraction leads to varying degrees of limitation of use of healed areas and is thus unfavorable.

3. Assessment of the newly formed granulation tissue—Since the evaluation of collagen synthesis is precluded in burn wound models, the newly formed granulation tissue in each burn wound was assessed histologically on PBD 12. Four adjacent sections were taken from the center of each wound. Employing the Mason's Trichrome staining method aided to delineate the newly formed granulation tissue which originated from the non-burned dermal layer in each section.

4. Hair follicle count—The preservation of hair follicles and their count was quantified. The presence of hair follicles and their regeneration indicated preservation of blood circulation and the degree of healing of the underlying tissues of the dermis.

Results

1. Epithelializtion—Tables 5 and 6—is clearly superior in the wounds receiving Compound 23 treatment being 50.1% to 81.4% for various Compound 23 concentrations, as compared with the average of 36.2% of the control wound (34.4% and 38.6% accordingly) which were treated with either BSA or saline only. Catalase treatment prevented new epithelial formation almost completely—and most of the wound remained unhealed.

2. Contraction—is a natural process occurring in each healing wound and too much contraction during healing may cause organ dysfunction. The results in Tables 5 and 6 indicate that Compound 23, particularly in the higher concentration, did not enhance contraction and may actually somewhat reduce this process.

3. Granulation tissue formation—In the five control wounds and three Compound 23 treated wounds analyzed from experiment no. 3, the thickness of the newly formed collagen in controls was 539 on the average whereas in Compound 23 treated wounds it was 467. This constitutes 86% of the collagen formed in untreated healing indicating that Compound 23 does not cause and any reduce fibrosis. This means that the compound reduces the amount of scar tissue and allows more normal tissue to be formed in the treated wounds.

4. Hair Follicle Count—The presence of hair follicles indicates maintenance of dermal microcirculation and, prevention of tissue ischemia and thus ischemic and postischemic damage. The preservation of hair follicles and their count were undertaken; the number of regenerated hair follicles were counted microscopically in tissue sections. The biological section was projected onto a video, colored screen, connected to a color camera. Hair follicles were counted in each wound, in three to eight microscopic fields,, in each of 4–8 histological sections. Each field was 2 mm long and 5 microns thick. The mean and standard error (SE) were calculated for each wound and for the whole treatment group. See especially Tables 8, 9 and 10 which appear hereinafter.

TABLE 5

| experiment no. 3 (10 animals - 20 wounds) | | | |
|---|---|---|---|
| | Epithelialization % | | |
| | E1 | E2 | Contraction % |
| control | 34.4 | 21.3 | 35.8 |
| Compound 23 3 mg/ml | 50.1 | 31.7 | 35.7 |
| catalase | 6.1 | 2.8 | 41.4 |

TABLE 6

| experiment no. 4 (11 animals - 22 wounds) | | | |
|---|---|---|---|
| | Epithelialization % | | |
| | E1 | E2 | Contraction % |
| control | 38.6 | 22.5 | 40.1 |
| Compound 23 3 mg/ml | 81.4 | 51.6 | 37.5 |
| Compound 23 3/2/1 mg | 61.3 | 33.6 | 42.1 |

In the subsequent experiment no. 5, we used 20 guinea pigs and inflicted 32 wounds. 14 control wounds were treated with saline. 9 wounds were treated with Compound-64 (3.8 mg/ml). 9 wounds were treated with Compound-23 mg/ml.

Table 7 summarizes the results of this experiment, with respect to % epithelialization and % contraction.

TABLE 7

| | experiment no. 5 | |
|---|---|---|
| | % Epithelialization = E1 | % Contraction |
| control | 69.2* | 44.4 |
| Compound 64 3.8 mg | 97.3** | 42.1 |
| Compound 23 | 91.3** | 37.0 |

*higher control values over previous experiments due to changed frequency of application of dressings.
**virtually total recovery With respect to epithelialization the two compounds 23 and 64 show considerable improvement as compared to untreated. Contraction was significantly changed by the treatments.

The following Tables 8, 9 and 10 each summarizes all the parameters which were assessed for experiments #3, #4, #5 respectively.

There was no substantially significant difference in the initial wound size among the treatment groups of each experiment as should be expected.

Contraction was significantly different amongst the various treatment groups in experiments #3 and #4 However, in experiment #5 contraction was significantly lower in the Compound 23 treated group as compared to controls (Table 7).

Contraction is a natural process occurring in each healing wound. Excessive contraction may lead to varying degrees of organ 1 imitation and is thus unfavorable. Contraction with the various treatments given and especially with compound 23 did not exceed control values and was actually reduced in experiment #5. This indicates that the drug does not heal by producing excessive fibrosis. A fibrotic scar is less aesthetic and limits the functionality of the healed area.

In experiment #3 (Table 8) epithelialization was only 6% in catalase treated group, 34.4% for control-B5A treated wound and. 50% for compound 23. Epithelialization with compound 23 treatment was superior to control treated wounds, it was not statistically significant. Thus catalase treatment was significantly worse than either the control or compound 23 treatments.

In experiment #4 (Table 9) treatment with 3 mg of compound 23 significantly improved. epithelialization to 89% as compared with 38.5% in control treated wounds. The use of decreasing amounts of compound 23 (treatment C) also improved e. pithelialization, but to a lesser degree.

In experiment #5 (Table 10) the wound dressings were not changed on the 4th day, but only on the 8th and 12th PBD The reduced dressing in experiment #5 resulted in improved healing of the wounds of all groups compared with experiments #3 and #4. Epithelialization with 3mg of compound 23 was 90.3%, meaning that wounds were almost completely healed on day 12. Another Co compound was introduced, compound 64, and it also dramatically improved epithelialization to 97%.

Across the three experiments reported hereinabove, epithelializaton was superior in all the groups treated with Co compounds. This should be considered in light of the crucial role of epithelialization in the process of healing.

Hair follicle preservation and formation is crucial in the assessment of wound healing since it also indicates the maintenance of dermal microcirculation and prevention of tissue ischemia.

Hair follicle preservation in experiment #3 (Table 8) was very significantly better with compound 23 than either catalase or control treated groups, the amount of hairs per field microscopic was twice as much in the compound 23 treated group; 15.5 in compound 23 vs. 8.2 and 9.2 in control and catalase treatments, respectively.

Experiment #4 (Table 9) exhibited the same phenomenon, 3 mg of compound 23 and decreasing amounts of compound 23 were superior to the control group, though treatment with a higher compound 23 concentration was superior to decreasing amounts of the same treatment, i.e. 15.4 and 13.1 hair follicles per field of compound 23 treated groups respectively vs. 6.9 hair follicles for control. Very surprisingly compound 64, which proved to be an inducer of epithelialization, did not improve hair follicle preservation over control values, and was significantly lower than treatment with compound 23.

Across the three experiments reported hereinabove compound 23 proved superior with respect to hair follicle preservation and this coincided with superior epithelialization, which represents healing on a macroscopic level. Hair follicle preservation was two-fold higher than control or any other treatment suggesting that microcirculation injury and ischemia resulting from superoxide radical production were at least partially prevented by the use of compound 23 as superoxide radical scavenger.

The thickness of the newly formed granulation tissue on PBD 12 was not fully assessed but in both experiments 3 and 4 (Tables 8, 9) the collagen formed in the compound 23 treated group was slightly thicker (10% to 15%) than control values a difference which was not statistically significant. The fact that the layer of new collagen did not exceed that of control by more than 10% to 15% taken together with the fact that contraction was lower due to treatment indicates that a more aesthetic scar will result from our treatment with compound 23.

The data indicate that burn wound healing in this guinea pig model was significantly accelerated in the groups treated especially with Co-compounds, i.e. compounds 23 and 64. This improvement was accompanied by a significant increase in epithelialization. Moreover, compound 23 also demonstrated improved hair follicle preservation, a fact which indicates that the microcirculation in the burn area was at least partially protected and therefore regenerated better during the healing process. The fact that contraction and new granulation tissue did not increase by compound 23 indicates that the scar tissue will not become excessively fibrotic and thus will result in a more aesthetic scar and a more functional healing organ.

TABLE 8

Assesment of burn wound healing by means of contraction, epithelialization, hair follicle preservation, and newly formed granulation tissue.

exp. 3
Female guinea pigs = 10, wounds (n) = 20
Weight = 530 + 10 gr.
Treatments:  A (n = 6) catalase          1 mg/ml/treatment
             B (n = 7) BSA = control     1 mg/ml/treatment
             C (n = 7) Co-BAE-23         3 mg/ml/treatment

| | Treatment | | |
|---|---|---|---|
| | A Catalase | B BBA = control | C Co-BAE-23 |
| Initial wound size - mm² | 1249.13 ± 25.64 | 1283.4 ± 68.7 | 1267 ± 37.94 |
| Contraction PBD-12(%) | 41.47 ± 4.73 | 35.83 ± 4.04 | 35.71 ± 2.42 |
| Epithelialization PBD-12(%) | 6.05 ± 6.05 | 34.4 ± 11.50 | 50.06 ± 12.14* |
| Hair follicles per 2 mm × 5 | 9.25 ± 3.3 | 8.18 ± 2.15 | 15.5 ± 1.38** |
| Hair follicles % of control | 113.4 | 100 | 189** |
| New collagen - | not assessed | 654.6 ± 16.0 | 730.72 − 44.6 |

* = statistically significant difference from control
** = very significant difference from control

TABLE 9

Assessment of burn wound healing, by means of contraction, epithelialization, hair follicle preservation, and newly formed granulation tissue.

exp. 4
Male animals = 11, wounds (n) = 22
Weight = 602.7 ± 24 gr.
Treat-   A (n = 8) Co-BAE-23     3 mg/ml/treatment
ments:   B (n = 7) control -     1 ml/treatment
         saline
         C (n = 7) Co-BAE-23     3 mg/ml/treatment 1-4 PBD
                                 2 mg/ml/treatment 5-8 PBD
                                 1 mg/ml/treatment 9-12 PBD

| | Treatment | | |
|---|---|---|---|
| | A Co-BAE-23 3 mg | B Saline control | C Co-BAE-23 3/2/1 mg |
| Initial wound size - mm² | 1466.23 ± 77.08 | 1435.74 ± 53.19 | 1566.13 ± 105 |
| Contraction PBD-12(%) | 36.14 ± 2.89 | 40.08 ± 1.88 | 42.13 ± 2.94 |
| Epithelialization PBD-12(%) | 89.25 ± 5.38** | 38.55 ± 11.60 | 52.56 ± 16.21* |
| Hair follicles per 2 mm × 5 | 15.4 ± 0.9** | 6.9 ± 2.06 | 13.1 ± 2.72* |
| New collagen - | 616.6 ± 46 | 576.5 ± 22.3 | 675.3 ± 79 |

* = some statistical significance from control
** = very significant difference from control

TABLE 10

Assessment of burn wound healing, by means

TABLE 10-continued of contraction, epithelialization, hair follicle preservation, and newly formed granulation tissue.

exp. 5
Female animals = 20, wounds (n) = 32
Weight = 532.5 + 6.02 gr.
Treatments: A (n = 9) Co-BAE-64   3.0 mg/ml/treatment
B (n = 14) control - saline   1 ml/treatment
C (n = 9) Co-BAE-23   3 mg/ml/treatment

| | Treatment | | |
|---|---|---|---|
| | A BBAE-64 | B Saline control | C Co-BAE-23 |
| Initial wound size - mm$^2$ | 1384.76 ± 35.7 | 1398 ± 34.1 | 1294.0 ± 33.9 |
| Contraction PBD-12(%) | 42.03 ± 1.89 | 44.89 ± 3.01 | 38.4 ± 3.17** |
| Epithelialization PBD-12(%) | 97.29 ± 1.51** | 69.25 ± 4.5 | 90.3 ± 5.33** |
| Hair follicles per 2 mm × 5 | 9.9 ± 0.83** | 10.6 ± 1.25 | 15.3 ± 2.39** |
| Hair follicles % of control | 93.4 | 100 | 144** |
| New collagen - | not assessed | not assessed | not assessed |

| | Treatment | | |
|---|---|---|---|
| | A C-23 | B C-67 | C Saline |
| Initial wound size - mm$^2$ | 1171.84 ± 132 | 1117.6 ± 58.1 | 1107.37 ± 125.23 |
| Contraction PDN-16% | 29.16 ± 11.09 | 26.23 ± 9.42 | 29.07 ± 6.8 |
| Epithelialization PBD-16(%) (E1) | 57.5 ± 29.4 | 69.17 ± 12 | 57.4 ± 18.98*(a) |
| Epithelialization PBD-16(5) (E2) | 38.98 ± 31.74 | 50.81 ± 11.21 | 41.8 ± 12.05*(b) |

Epithelialization (E1) - represents the % of the newly covered area of the wound surface on the 16th post burn day out of the total wound area on the same day.
Epithelialization (E2) - represents the % of the newly covered area of the wound surface on the 16th post burn day out of the initial wound area on the first day.
** = very significant difference
*marginally statistically significant from control.

The following examples are directed to the preparation of pharmaceutical composition for the typical treatment of burns.

EXAMPLE I

An aerosol composition is prepared having the following proportions:

| | |
|---|---|
| Benxocaine | 1.00% |
| Camphor | 0.10 |
| Menthol | 0.10 |
| Pyrilamine Maleate | 0.25 |
| Bacitracin | 0.02 |
| Acetulan$^R$ (Acetylated landin alcohols) | 1.00 |
| Oleyl Alcohol | 4.00 |
| Dipropylene Glycol | 1.00 |
| Compound 23 | 0.3 |
| Propellant 152 a/II | 92.23 |
| | 100.00% |

EXAMPLE II

The following water-soluble ointment is prepared having the following proportions:

| Polyethylene Glycol 200 | |
|---|---|
| Monostearate | 15.0% |
| Veegum | 5.0 |
| Polysorbate 80 | 1.0 |
| Methylparaben | 0.1 |
| Compound 23 | 0.3 |
| Purified water | 78.6 |
| | 100.00% |

EXAMPLE III

The following oleaginous ointment is prepared having the following proportions:

| | |
|---|---|
| Compound 64 | .38% |
| Petrolatum balance to 100% | |

V. Evaluation of the potential of compound 23 in the presence of human serum:

Material and Methods

The microorganisms, growth conditions, MIC and MBC tests were performed in the same conditions as in the first parts. But instead of using BH and TSB as growth media sterile, human serum was used. The microorganisms were incubated in human serum with different concentrations of compound 23, for establishing the MIC, while the MBC was determined on TSA as before.

Results and Discussion

The results summarized in Table 12 indicate that:

1) The gram (−) microoganisms show the same pattern as if they were grown in the rich medium (BH), the MBC is 4 mg/ml approximately.

2) The gram (+) microorganisms grown in the serum are as sensitive as those grown in BH except for Staph. Coagulase positive which is less sensitive in sterum (MBC+3.2 mg/ml). The reason may be that this microorganism is able to coagulate the serum and thereby influence the mode of action of compound 23.

TABLE 12

Sensitivity of gram positive and gram negative bacteria to C$_{23}$ compound grown in human serum.

| Microorganism C$_{23}$ (mg/ml) | Strep. β hemolytic MBC* | Strep. α hemolytic MBC | Enterococci MBC | Staph. coagulase (+) MBC | Staph. coagulase (−) MBC |
|---|---|---|---|---|---|
| 0.4 | 5.10$^4$ | 3.10$^4$ | 4.10$^3$ | 5.10$^4$ | 1.10$^4$ |
| 0.8 | 1.10$^4$ | 5.10$^2$ | 4.10$^2$ | 1.10$^4$ | 1.10$^3$ |
| 1.6 | 8.10$^3$ | 1.10$^2$ | 2.10$^2$ | 1.10$^3$ | 5.10$^2$ |
| 3.2 | 5.10$^3$ | 5.10$^1$ | 2.10$^1$ | 1.10$^2$ | 2.10$^2$ |
| 6.4 | 1.10$^2$ | 1.10$^1$ | 1.10$^1$ | 1.10$^1$ | 1.10$^1$ |

| Microorganism C$_{23}$ (mg/ml) | E. coli MBC | Klebsiella MBC | Pseudomonas MBC | Proteus MBC | C. albicans MBC |
|---|---|---|---|---|---|
| 2 | 8.10$^3$ | 8.10$^3$ | 8.10$^3$ | 3.10$^3$ | 3.10$^3$ |
| 4 | 8.10$^2$ | 2.10$^2$ | 7.10$^3$ | 4.10$^2$ | 1.10$^3$ |
| 8 | 6.10$^1$ | 3.10$^1$ | 1.10$^3$ | 8.10$^1$ | 1.10$^2$ |

TABLE 12-continued

| Sensitivity of gram positive and gram negative bacteria to $C_{23}$ compound grown in human serum. | | | | | |
|---|---|---|---|---|---|
| 16 | 0 | 0 | $1.10^2$ | $1.10^1$ | $1.10^2$ |

*MBC = Minimal Bactericidal Concentration.
The initial concentration of microorganisms was $5.10^4$/ml.

VI. Comparison of the sensitivity of ten different strains of clinical isolates of Psedomonas and the strain of Staph. coagulase positive to compound 23:

The purpose of these experiments was to compare ten strains of Pseudomonas and Staph. (+) which showed various patterns of sensitivity to antibiotics, to their sensitivity to compound 23 compositions.

Material and Methods

Microorganisms—Ten clinical isolates of Pseudomonas aeruginosa and ten of Staph. (+) with various patterns of sensitivity to antibiotics were tested.

Growth conditions—As mentioned in the first part, but were tested only on TSB medium.

MIC and MBC—as described above.

Results and Discussion

Although many of the strains tested (Pseudomonas as well as Staph. coagulase positive) were very resistant to many antibiotics tested (as Gentamcin, and all the new cephalosporins), their sensititivity to compound 23 compositions was very similar (Table 13). Compound 23 for Pseudomonas was bactericidal at 4 mg/ml, whereas for Staph. (+) it was bactericidal 1.5 mg/ml–3.0 mg/ml.

Sensitivity of various microorganisms were tested to:
(a) Silver sulfadiazine (SSD)
(b) Sulfamylon (SM)
(c) Compound 23.

The purpose of this study was to compare the sensitivity of SSD and SM, which are well known antimicrobial agents, to compound 23.

The microorganisms, growth conditions, MIC and MBC tests are performed as described in the first part, on TSB medium.

Results and Discussion

Silver Sulfadiazine is effective against the strains tested (gram positive and negative as well) at low concentration (bactericidal at 50 µg/ml) in comparison with compound 23 (Table 14).

But Sulfamylon is effective at low concentrations (75-150 µg/ml) only for the Streptococci, whereas for the other gram (+) bacteria tested (namely, Staphylococci or Enterococci) or gram. (−) bacteria very high concentrations are needed to be used to get a bactericidal effect (12,000 µg/ml). This concentration is much higher than that of compound 23. *C. albicans* is not sensitive even at that concentration.

TABLE 13

Sensitivity to C-23 of various strains of clinical isolates (a) Pseudomonas

| Microorganism | Ps.(1) | | Ps.(2) | | Ps.(3) | | Ps.(4) | | Ps.(5) | |
|---|---|---|---|---|---|---|---|---|---|---|
| $C_{23}$ mg/ml | MIC[1] | MBC[2] | MIC | MBC | MIC | MBC | MIC | MBC | MIC | MBC |
| 2 | − | $4.10^4$ | − | $5.10^4$ | − | $4.10^4$ | − | $3.10^4$ | − | $5.10^4$ |
| 4 | − | $1.10^3$ | − | $4.10^4$ | − | $1.10^2$ | − | $1.10^3$ | − | $1.10^3$ |
| 8 | − | $2.10^2$ | − | $1.10^1$ | − | 0 | − | 0 | − | 0 |
| 16 | − | 0 | − | $1.10^1$ | − | 0 | − | 0 | − | 0 |

| Microorganism | Ps.(6) | | Ps.(7) | | Ps.(8) | | Ps.(9) | | Ps.(10) | |
|---|---|---|---|---|---|---|---|---|---|---|
| $C_{23}$ mg/ml | MIC | MBC | MIC | MBC | MIC | MBC | MIC | MBC | MIC | MBC |
| 2 | − | $1.10^4$ | − | $5.10^4$ | − | $2.10^4$ | + | $1.10^4$ | + | $2.10^4$ |
| 4 | − | 0 | − | $2.10^3$ | − | $6.10^3$ | − | 0 | − | $8.10^1$ |
| 8 | − | 0 | − | 0 | − | 0 | − | 0 | − | 0 |
| 16 | − | 0 | − | 0 | − | 0 | − | 0 | − | 0 |

(b) *Staph. coagulase* positive

| | Staph(+) 1 | | 2 | | 3 | | 4 | | 5 | |
|---|---|---|---|---|---|---|---|---|---|---|
| | MIC | MBC | MIC | MBC | MIC | MBC | MIC | MBC | MIC | MBC |
| 0.2 | + | | + | | + | | + | | + | |
| 0.4 | + | | + | | + | | + | | + | |
| 0.75 | + | | − | $8.10^3$ | + | | + | | − | $1.10^4$ |
| 1.5 | − | $1.10^4$ | − | 0 | − | $4.10^4$ | − | $4.10^1$ | − | $6.10^1$ |
| 3 | − | 0 | − | 0 | − | $6.10^2$ | − | 0 | − | 0 |

| | 6 | | 7 | | 8 | | 9 | | 10 | |
|---|---|---|---|---|---|---|---|---|---|---|
| | MIC | MBC | MIC | MBC | MIC | MBC | MIC | MBC | MIC | MBC |
| 0.2 | + | | − | $3.10^4$ | − | $2.10^4$ | − | $8.10^4$ | − | $5.10^4$ |
| 0.4 | + | | − | $1.10^4$ | − | $8.10^3$ | − | $1.10^4$ | − | $9.10^3$ |
| 0.75 | − | $2.10^4$ | − | $1.10^4$ | − | $6.10^3$ | − | $1.10^4$ | − | $9.10^3$ |
| 1.5 | − | $8.10^3$ | − | $8.10^3$ | − | 0 | − | $1.10^4$ | − | $3.10^3$ |
| 3 | − | $1.10^2$ | − | $1.10^2$ | − | 0 | − | $8.10^3$ | − | $1.10^2$ |

1. MIC + Minimal Inhibitory Concentration. (=) visible/growth; (−) transparent.
2. MBC = Minimal Bactericidal Concentration.
The initial concentration of microorganisms was $5.10^4$/ml.

TABLE 14

Sensitivity of gram positive and gram negative bacteria to Silver Sulfa Diazine SSD and Sulfamylon SM.

| Microorganism SSD μg/ml | Strep. β MIC[1] | MBC[2] | Strep. α MIC | MBC | Enterococci MIC | MBC | Staph (+) MIC | MBC | Staph (−) MIC | MBC |
|---|---|---|---|---|---|---|---|---|---|---|
| 25 | − | $7.10^4$ | − | $7.10^4$ | + | | + | | + | |
| 50 | − | $7.10^3$ | − | $8.10^1$ | + | | − | $7.10^3$ | − | $5.10^4$ |
| 75 | − | 0 | − | 0 | − | $7.10^4$ | − | $1.10^3$ | − | $1.10^3$ |
| 100 | | | | | | | | | | |
| 150 | | | | | | | | | | |

| Microorganism SSD μg/ml | E. coli MIC | MBC | Klebsiella MIC | MBC | Pseudomonas MIC | MBC | Proteus MIC | MBC |
|---|---|---|---|---|---|---|---|---|
| 25 | | | | | | | | |
| 50 | − | $8.10^3$ | − | $1.10^3$ | − | $5.10^4$ | − | 0 |
| 75 | − | $2.10^2$ | − | 0 | − | $3.10^3$ | − | 0 |
| 100 | − | 0 | − | 0 | − | $3.10^1$ | − | 0 |
| 150 | − | 0 | | 0 | − | 0 | | 0 |

| Microorganism SM μg/ml | Strep. β MIC[1] | MBC[2] | Strep. α MIC | MBC | Enterococci MIC | MBC | Staph (+) MIC | MBC | Staph (−) MIC | MBC |
|---|---|---|---|---|---|---|---|---|---|---|
| 75 | − | $2.10^3$ | − | | | | | | | |
| 150 | − | $9.10^2$ | − | $1.10^3$ | | | | | | |
| 300 | − | $6.10^2$ | − | $1.10^3$ | | | | | | |
| 600 | − | $6.10^2$ | − | $1.10^3$ | | | | | | |
| 3000 | | | | | + | $1.10^4$ | − | $1.10^4$ | − | $1.10^4$ |
| 6000 | | | | | − | $1.10^4$ | − | $1.10^4$ | − | $1.10^4$ |
| 12,000 | | | | | − | $5.10^3$ | − | $5.10^3$ | − | $3.10^3$ |

| Microorganism SSD μg/ml | E. coli MIC | MBC | Klebsiella MIC | MBC | Pseudomonas MIC | MBC | Proteus MIC | MBC |
|---|---|---|---|---|---|---|---|---|
| 75 | | | | | | | | |
| 150 | | | | | | | | |
| 300 | | | | | | | | |
| 600 | | | | | | | | |
| 3000 | + | | + | | + | | + | |
| 6000 | − | | − | | − | | + | |
| 12,000 | − | $1.10^4$ | − | $1.10^4$ | − | $1.10^4$ | − | $1.10^4$ |

1. MIC = Minimal Inhibitory Concentration. (+) visible growth; (−) transparent.
2. MBC = Minimal Bactericidal Concentration.
The initial concentration of microorganism was $5 \times 10^4$/mL VII. Mutagenicity of compounds #23 and 64:

Test was carried out on Photobacterium fisherii as described in Methods in Enzymology Vol. 133:264–284(1986) by S. Ulizur who also carried out the present tests. This test is more sensitive than the Ames test (see reference).

| Conc. in mg/ml | #23 growth | luminescence | #64 growth | luminescence |
|---|---|---|---|---|
| 10 | − | 0 | − | 0 |
| 5 | − | 0 | − | 0 |
| 2.5 | − | 0 | − | 0 |
| 1.25 | − | 0 | − | 0 |
| 0.6 | − | 0 | − | 0 |
| 0.3 | − | 0 | − | 0 |
| 0.15 | − | 0 | − | 7 |
| 0.075 | − | 0.5 | + | 130 |
| 0.037 | ++ | 500 | ++ | 300 |
| control 0 | ++ | 800 | ++ | 800 |

Conclusion: These compounds are efficient antimicrobials to this gram-negative bacterium. No mutagenic activity is revealed by back mutation to luminescent state.

The values are given as luminescence (quanta/sec$^{-1}$/ml$^{-1}$). Significant genotoxic effect of a compound is considered when the maximal luminescence developed due to the chemical in question is 3–4 times higher than that obtained with the control.

VIII. Activity of Compounds Outside Defined Class:

The following compounds were found to be unreactive, meaning they show no scavenging activity below concentrations of about $10^{-2}$ M:

Co(en)$_3$Cl$_3$. 3H$_2$O (where en=ethylenediamine);
Co(pn)$_3$Cl$_3$ (where pn=propylenediamine);
[Co(Tim-6,13-(OH)$_2$)Br$_2$]Br (the compound is shown below and is also toxic);

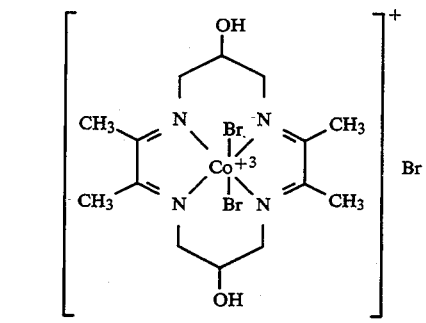

Cis-α[Co(trien)Cl$_2$]Cl (where trien = diethylenetriamine);

Ferrocene and Ferrocene derivatives (very effective as O$_2$$^−$ scavengers but has absolutely no biological activity. In burn wounds, these compounds are worse than the controls).

REFERENCES

1. G. Costa, G. Mestroni. G. Tauzer and L. Stefani, Journal of Organometallic Chemistry, 1966, 6, 181-187.
2. J. P. McCarthy, R. J. Hovey, K. Ueno, A. E. Martell, J.A.C.S., 1955, 77, 5820-5824.
3. K. Kasuga, T. Nagahara, A. Tsuge, K. Sogabe, Y. Yamamoto, Bull. Chem. Soc. Jpn, 1983, 56, 95-98.
4. T. Nagahara, K. Kasuga and Y. Yamamoto, Inorg. Nucl. Chem. Letters, 1981. 17, 7-8, 235; k. Kasuga, Y. Iida, Y. Yamamoto, M. Aihara and M. Kudo, Inorganica Chimica Acta, 1984, 84, 113; T. Nagahara, K. Kasuga and Y. Yamamoto, Inorganica Cimica Acta, 1981, 47, 37.
4. A. W. Johnson, E. Markham and R. Price, Org. Synth., Collective volume V, 785.
6. W. Dieckman, Chem. Ber., 1912, 2689.
7. R. S. Drago and B ,. R. Corden, Acc. Che. Res., 1980, 13, 353.
8. E. C. Niederhoffer, J. H. Timmons and A. E. Martell, Chem. Rev., 1984, 84, 137.
9. A. Summerville, R. D. Jones, B. M. Hoffman and F. Basolo, J. Chem. Educ., 1979, 56, 3, 157.
10. D. Getz, E. Melamud, B. L. Silver and Z. Dori, J. Am. Chem. Soc., 1975, 97, 3846.

What is claimed is:

1. A pharmaceutical composition comprising a pharmaceutically acceptable carrier and a complex in an amount effective to alleviate undesirable symptoms associated with the presence of free radicals, the complex comprising a Co(Ill) complex having an octahedral basal plane defined by four donor atoms A, which may be same or different, and two axial ligand donor atoms B, which may be the same or different, said donor atoms having a low to intermediate ligand field strength, said complex reacting with $O_2-$ to form a $Co(Ill)-O_2$ adduct or oxidizing $O_2-$ to produce dioxygen and a Co(II) complex.

2. The pharmaceutical composition of claim 1 wherein the complex has a quadridentate ligand L bound to the Co(III) through the donor atoms which imposes planarity on the octahedral basal plane.

3. The pharmaceutical composition of claim 2 wherein the quadridentate ligand L and bonded Co(III) comprises a 6,5,6 ring system, said 6-membered ring of said 6,5,6 ring system being unsaturated.

4. The pharmaceutical composition of claim 3 wherein the complex has the formula $[CoL(B)_2]^2$ wherein B is selected from the group consisting of $I^-$, $Br^-$, $Cl^-$, $F^-OH^-$, $C_2O_4^{2-}$, $H_2O$, and $NH_3$, and n is $-1$, 0, or $+1$.

* * * * *